United States Patent [19]

Hofmann

[11] Patent Number: 4,910,223
[45] Date of Patent: Mar. 20, 1990

[54] LOW VISCOSITY SOLVENT MIXTURE FOR DISSOLUTION OF CHOLESTEROL GALLSTONES

[75] Inventor: Alan F. Hofmann, La Jolla, Calif.

[73] Assignee: The Regents of the University of California, Berkeley, Calif.

[21] Appl. No.: 157,656

[22] Filed: Feb. 19, 1988

[51] Int. Cl.$^4$ .................. A61K 31/23; A61K 31/08
[52] U.S. Cl. ................................. 514/552; 514/722
[58] Field of Search .................. 514/552, 546, 722

[56] References Cited

U.S. PATENT DOCUMENTS 4,205,086 5/1980 Babayan ............................. 514/552

OTHER PUBLICATIONS

Allen et al. (I), *Gastroenterology*, 89, 5, 1097 (Nov., 1985).
Allen et al. (II), *Gastroenterology*, 88, 1, 122 (Jan., 1985).
Bogardus, *J. Pharm. Sci.*, 73, 7, 906 (Jul., 1984).
Palmer et al., *Gut*, 27, 2, 196 (Feb., 1986).
Thistle et al., *Gastroenterology*, 78, 5, 1016 (May, 1980).

*Primary Examiner*—Douglas W. Robinson
*Assistant Examiner*—Raymond J. Henley, III
*Attorney, Agent, or Firm*—Brown, Martin, Haller & McClain

[57] ABSTRACT

A composition is described for the dissolution of cholesterol gallstones, which composition is a mixture of monooctanoin and diethyl ether and has a viscosity of not more than 7 cp and can be maintained in the body at a temperature below its boiling point. The volumetric ratio of monooctanoin:diethyl ether will usually be in the range of about 10:90 to about 70:30. The composition can be infused by a variety of techniques including high flow low pressure pumps.

16 Claims, 2 Drawing Sheets

LOW VISCOSITY SOLVENT MIXTURE FOR DISSOLUTION OF CHOLESTEROL GALLSTONES

FIELD OF THE INVENTION

The invention herein relates to medical treatments for the contact dissolution of cholesterol gallstones. More particularly it relates to low viscosity pumpable solvents for such treatments.

BACKGROUND OF THE INVENTION

The contact dissolution of cholesterol gallstones in human patients is a well recognized medical procedure and may be favored over surgical procedures to remove the gallstones in patients at increased risk for surgery; see, e.g., U.S. Pat. No. 4,205,086. The dissolution procedures normally involve infusion of the solvent into the biliary tract by means of a T-tube, nasobiliary tube, percutaneous transhepatic catheter or cholecystostomy tube by use of a constant infusion pump or by gravity or by manual repeated instillation and withdrawal using a syringe; see Palmer et al, Gut, 27, 2, 196 (1986). Frequently the stones fragment during the dissolution procedure, which advantageously increases the rate of dissolution.

A number of different types of solvents have been used or suggested for the dissolution procedure. These include organic solvents or liquids such as diethyl ether, chloroform or d-limonene as well as aqueous micellar solutions of bile salts. The aforementioned U.S. Pat. No. 4,205,086 also lists a large number of useful liquid fatty acids and the alcohol ethers thereof.

One solvent which has shown efficacy for dissolving cholesterol gallstones is monooctanoin, which is an esterified reaction product of glycerol and octanoic acid; see the aforementioned Gut article as well as Thistle et al, Gastroenterology, 78, 1016 (1980). Studies in vitro and in vivo have shown the ability of monooctanoin to significantly reduce and/or eliminate cholesterol gallstones by dissolving them so that the dissolved material can be eliminated or removed from the body. Monooctanoin has been marketed as an orphan drug with the approval of the Food and Drug Administration.

It is known that the viscosity characteristics of the solvent are important in the dissolution procedure [see Bogardus, J. Pharm. Sci, 73, 906 (1984)] since gallstones dissolve only very slowly in highly viscous solvents. Materials such as monooctanoin which are themselves of high viscosity may be diluted in order to be capable of being used in the standard perfusion equipment, such as by being dissolved or dispersed in varying amounts of water; see the aforementioned U.S. Pat. No. 4,205,086 and Gut article. While effective to reduce the viscosity of the monooctanoin somewhat (Bogardus, supra reports that addition of up to 15% water, the essential maximum, reduced the monooctanoin viscosity from 48 cp to about 28–30 cp), the water has no significant therapeutic effect in the gallstone dissolution treatment. Improvement in the dissolution efficacy obtained by dilution of the monooctanoin is slight.

The use of ethers to dissolve cholesterol gallstones is known. Two ethers which are of interest are diethyl ether (ethoxyethane) and methyl t-butyl ether (MTBE). The principal advantage of diethyl ether is that it is approved for some therapeutic uses with humans, being the common "ether" of anesthesia. In the past, however, it has not been possible to use diethyl ether for in vivo gallstone reduction because of its low boiling point (34.5° C.) and high volatility. When instilled in the biliary tract, the liquid boils and the resultant ether vapor expands greatly in volume, leading to serious side effects of pain and nausea; Allen et al., Gastroenterology, 89, 5, 1097 (1985) ["Allen et al. (I)"]. MTBE also works well for dissolving gallstones in vitro and, in addition, has a satisfactory boiling point (55° C.), but is not approved for therapeutic use; Allen et al., Gastroenterology, 88, 1, 122 (1985) ["Allen et al. (II)"].

Recently there has been developed a novel infusion pump which produces a high flow rate at low pressure. This pump has been described and claimed in U.S. patent application Ser. No. 06/871,775 (filed June 9, 1986) by applicant S. Zakko. While this pump has proved quite efficacious for gallstone dissolution, its satisfactory performance depends on being used with relatively low viscosity solvents. Consequently, monooctanoin by itself, or monooctanoin diluted with small amounts of water (Gut, supra) cannot be used in this type of pump because of its high viscosity. Similarly, there are other instances the high viscosity of monooctanoin prevents its practical use as a perfusion solvent.

It would therefore be advantageous to have a solvent composition which incorporates therapeutically effective amounts of monooctanoin and diethyl ether, which has a viscosity low enough to be used in all types of perfusion devices and which has a boiling point which permits its use in the body. Both principal components of the composition will thus contribute therapeutically to the dissolution of the gallstones.

SUMMARY OF THE INVENTION

The invention herein is a low viscosity composition for the dissolution of cholesterol gallstones which comprises a mixture of monooctanoin and diethyl ether, and has a viscosity of not more than 7 centipoises and a boiling point greater than 35° C., which will permit it to be maintained in the body at a temperature below its boiling point. The compositions will normally have a monooctanoin:diethyl ether volumetric ratio in the range from about 10:90 to about 70:30, preferable a range of 10:90 to 50:50, with a particularly preferred composition having a ratio of 30:70.

The invention also encompasses a method of treating patients having common bile duct cholesterol calculi which comprises infusing into the biliary tract of the patient a composition comprising a mixture of monooctanoin and diethyl ether having a viscosity of not more than 10 cp and capable of being maintained in the body at a temperature less than its boiling point.

In other aspects the invention encompasses a method of dissolving common bile duct cholesterol calculi which comprises contacting the calculi with the aforesaid composition. In addition, the invention involves a method of reducing the viscosity of a therapeutically effective amount of monooctanoin and/or reducing the volatility (increasing the boiling point) of a therapeutically effective amount of diethyl ether, which comprises forming a mixture of sufficient volumes of monooctanoin and diethyl ether to produce a composition having a viscosity of not more than 7 cp and a boiling point of greater than 35° C. which is capable of being maintained in the body at a temperature below its boiling point.

All percentages and concentrations herein are by volume unless otherwise noted.

DETAILED DESCRIPTION AND PREFERRED EMBODIMENTS

Figure 1:
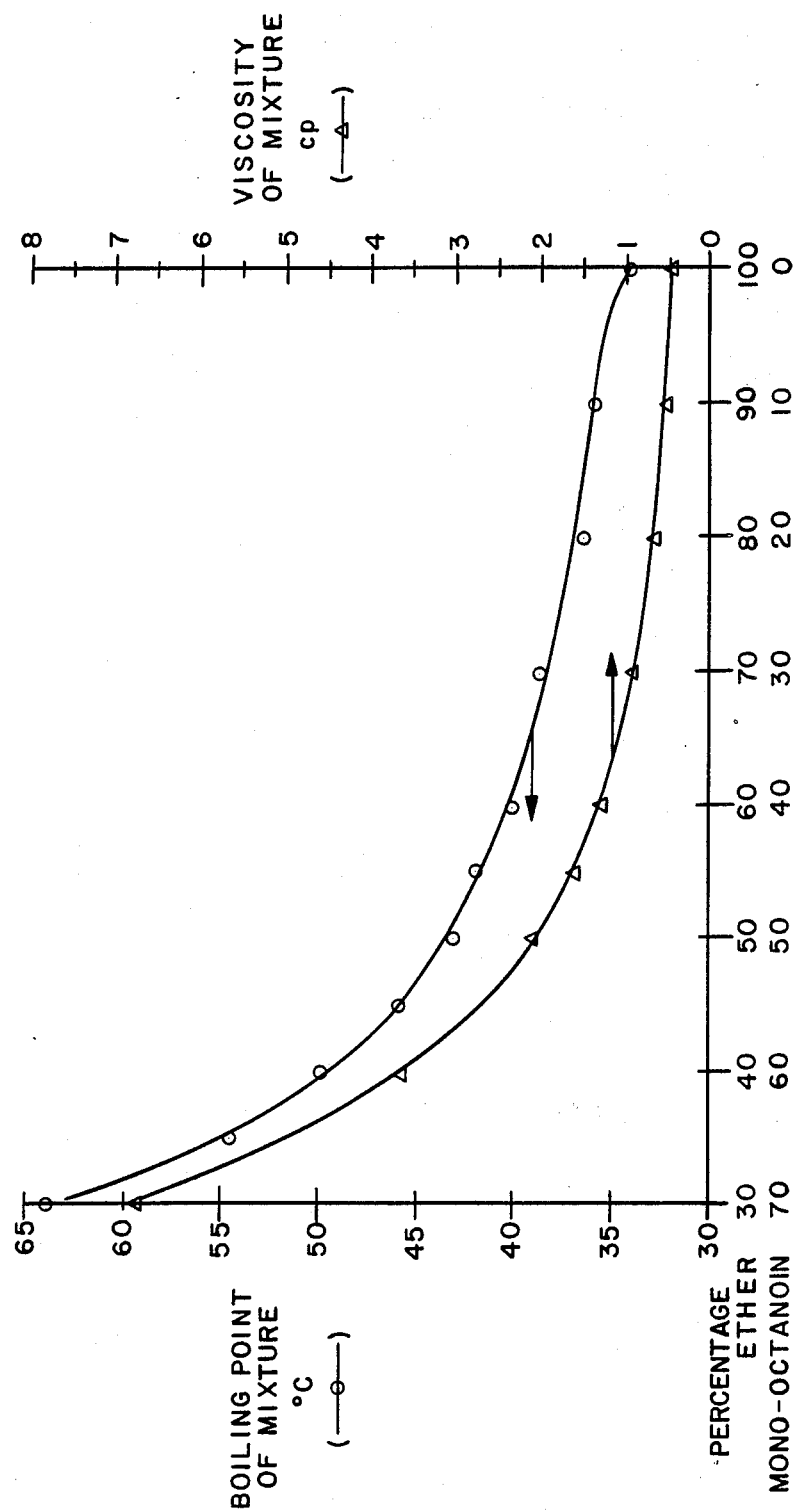
FIG. 1 is a graph showing the correlation between composition of the mixture and its boiling point in degrees Celsius (upper curve) or its viscosity in centipoises (lower curve).

The invention in its various aspects herein involves the surprising discovery that two materials, monooctanoin and diethyl ether, which are individually unsuitable in many or all instances for perfusion dissolution treatment of cholesterol gallstones or calculi, can be combined into a mixture which retains the advantageous properties of the components but eliminates their disadvantageous properties. In the composition of this invention the cholesterol dissolving properties of the monooctanoin and the diethyl ether are retained and available for effective use, while the excessive viscosity of the monooctanoin is reduced by the diethyl ether and the boiling point of the diethyl ether is increased by the monooctanoin. To the best of our knowledge, this synergistic combination of two otherwise unusable materials, and particularly the wide range of compositions over which this mixture has superior dissolving properties, has not previously been recognized.

Most importantly also, there is a significant improvement in the ability of the mixtures to dissolve cholesterol calculi, as compared to the individual compounds. This is quite unexpected since no suggestion of any such major effect appears in any of the prior art.

Monooctanoin is a semi-synthetic vegetable oil which is commonly formed by the reaction of octanoic acid and glycerol. The two reactants are heated until virtually all of the octanoic acid is esterified. While nominally the reaction product is considered to be entirely monooctanoin (glyceryl-1-monooctanoate), it is generally found that the reaction product is in fact a mixture composed of approximately 70% glyceryl-1-monooctanoate and about 30% glyceryl dioctanoate. Traces of glyceryl trioctanoate and octanoic acid may also be present, as well a small amounts of other organic compounds; Allen et al. (I), *supra*. The details of typical production of commercial monooctanoate may be found in the aforementioned U.S. Pat. No. 4,205,086. Monooctanoin has been commercially available under the trademarks "Capmul" and "Moctanin".

As noted above, monooctanoin has been reported by Bogardus, supra, to have a viscosity at 37° C. of about 48 cp. Dilution with water decreases that viscosity to about 25–30 cp at 10–18% water. Since the solubility of water in monooctanoin at 37° C. is only about 15%, no further decrease in viscosity can be expected by addition of more water. Similarly, while Bogardus reported that there can be an increase in dissolution rate of cholesterol in monooctanoin by addition of water, those reported data also show that at greater than 5% water content, the dissolution rate becomes constant and further water addition is of no effect.

Diethyl ether (ethoxyethane) is a common chemical of commerce. It is manufactured in commercial quantities by many chemical producers and its properties are widely reported. Of particular interest to this invention is its boiling point of 34.5° C. at 1 atmosphere as well as its high volatility. While its property of being in the gaseous state at ordinary body temperature (37° C.) makes it quite useful as an anesthetic, that has previously ruled out its use for in vivo gallstone dissolution.

We have now discovered that these two disparate materials can be combined into a highly effective low viscosity cholesterol gallstone solvent which can be readily infused into a patient's biliary tract by a wide variety of perfusion techniques, including syringes, the aforesaid pump or other devices commonly used by the medical community for the treatment of the calculi, and maintained in the body at a temperature below its boiling point. The composition thus provides the synergistic effect of two excellent solvents while avoiding the viscosity and volatility problems each possesses separately.

The concentration of the two components in the mixture is determined by two limiting factors: the maximum viscosity of 7 cp and a boiling point greater than 35° C. The viscosity limitation is critical; at higher viscosities the mixture becomes too viscous to be infused easily and to dissolve the gallstones in a reasonable length of time. In effect the mixture approaches the viscosity properties of anhydrous monooctanoin or the prior art monooctanoin/water mixtures, which require times on the order of 7–21 days to dissolve cholesterol gallstones. While the maximum acceptable viscosity of the mixture is 7 cp, preferably the mixture will have a viscosity of not more than 5 cp, and more preferably not greater than 2 cp.

The minimum boiling point limitation is based on the requirement that the mixture remain liquid at normal body temperatures so that it can be properly infused by liquid syringes, pumps or the like and will not vaporize internally from the patient's body heat. The minimum boiling point will be greater than 35° C., and preferably at least 37.5° C. Mixtures having a boiling point above 37° C. remain liquid in the patient's body under all normal conditions, since their boiling points are greater than the normal body temperature. However, we have also found that, even for mixtures with boiling points in the range of 35°–37° C., if the mixture is kept at ambient room temperature (about 25° C.) until it is perfused, its temperature during the time it remains in the body will not rise to the boiling point. Such compositions therefore may also be used successfully in this invention.

Based on these considerations, we have found that the appropriate mixtures will normally have a monooctanoin:diethyl ether volumetric ratio in the range of from about 10:90 to about 70:30, preferably 10:90 to 50:50 and most preferably about 30:70 (the last having the maximum cholesterol solubility and an excellent viscosity).

Figure 2:
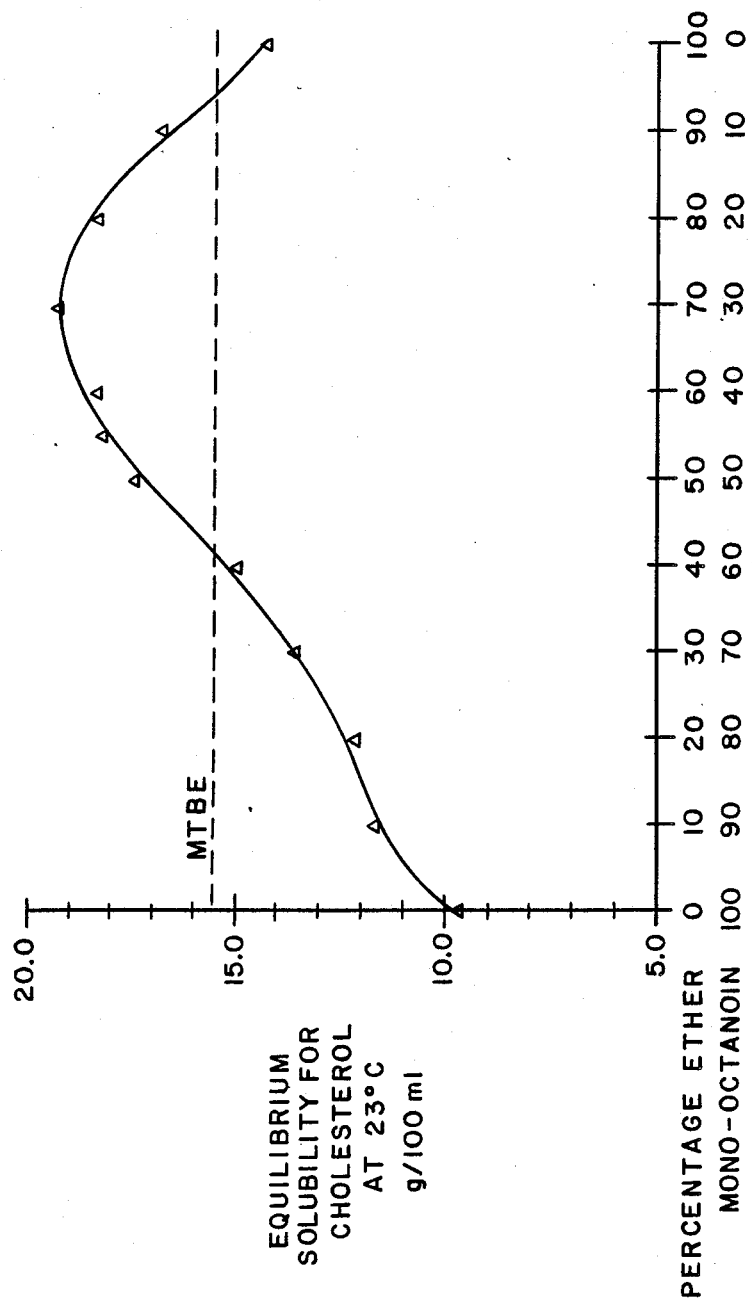
FIG. 2 is a graph showing the correlation between the composition of the mixture and its equilibrium solubility for cholesterol at 23° C. Comparison with the solubility of MTBE is also shown.

Table I below reflects the graphs of FIGS. 1 and 2, and presents data on a number of compositions of this invention which were formulated and their properties measured *in vitro*. Viscosity and cholesterol solubility were determined at 37° C.; boiling point was at 1 atmosphere. For comparison purposes, the same properties are shown in Table I for MTBE, water, anhydrous monooctanoin and a monooctanoin/15% water mixture.

TABLE I

| Composition, % by Volume | | Viscosity, | Boiling | Cholesterol Solubility, |
|---|---|---|---|---|
| MO(a) | DEE(a) | cp | Point, °C. | g/100 ml |
| 10 | 90 | 0.5 | 36 | 16.6 |
| 15 | 85 | 0.6 | 36 | 17.8 |
| 20 | 80 | 0.7 | 37 | 18.4 |
| 25 | 75 | 0.75 | 37 | 19.0 |
| 30 | 70 | 0.88 | 38 | 19.3 |
| 35 | 65 | 1.0 | 39 | 19.0 |
| 40 | 60 | 1.2 | 40 | 18.4 |
| 45 | 55 | 1.5 | 42 | 17.8 |
| 50 | 50 | 2.0 | 43 | 17.2 |
| 55 | 45 | 2.7 | 45 | 16.5 |
| 60 | 40 | 3.6 | 48 | 15.7 |
| 65 | 35 | 4.8 | 52 | 14.9 |
| 70 | 30 | 6.8 | 64 | 14.0 |
| MTBE | | — | 55 | 15.6 |
| Water | | 0.7 | 100 | insol. |
| MO, anhyd. | | 48(b) | — | 11.7 (c) |
| MO, anhyd. | | — | — | 8.7 (d) |
| MO/H$_2$O | | 28(b) | — | 8.2 (b) |

(a) MO = Monooctanoin  DEE = Diethyl ether
(b) reported by Bogardus, supra.
(c) reported by Thistle et al, supra.
(d) measured Several points which are important to this invention can be drawn from these data. First, and most surprisingly, it will be seen that over an extended range of formulations the compositions of this invention have substantially better cholesterol solubility properties than MTBE, which has previously been considered to be the efficacy standard (see Allen et al. I, *supra*), or monooctanoin alone. This superiority extends well into the high-ether-content formulations, which encourages the use of such formations. Secondly, these data show that the cholesterol dissolving properties of the compositions are substantially greater than that of monooctanoin alone, indicating that, unlike water as a component, diethyl ether is providing a significant therapeutic effect in the mixture. Further, these data indicate that it is possible to formulate mixtures of monooctanoin and diethyl ether in which the previous volatility and boiling point limitations of the diethyl ether and the viscosity problems of the monooctanoin are eliminated, while yet retaining the excellent cholesterol solubility properties of each and indeed combining those properties in a synergistic manner.

As an example of the present invention, a composition containing 40% monooctanoin and 60% diethyl ether was formulated. A large cholesterol gallstone having a diameter of approximately 1 cm and a weight of 1.6 g was hemisected and placed in a large test tube. The composition was circulated through the test tube using the above-mentioned Zakko pump at a flow rate of 250 ml/min. (By comparison, a pump reported in Allen et al. I, supra, which was specially designed to handle monooctanoin alone, could maintain only 90 ml/min, and that only on an intermittent basis.) The stone dissolved completely in 22.5 minutes indicating that the solvent was highly effective and its viscosity was sufficiently low to be readily pumped and circulated by the pump.

In related experiments with formulations ranging up to 10:90 monooctanoin:diethyl ether, similar results have been obtained. Notably, it has been shown that the dissolution rate of cholesterol gallstones can be reduced from a matter of days to a matter of minutes by using the compositions of this invention, as compared to prior art procedures. No problems were encountered with maintaining the temperature of the compositions below their boiling points during the entire perfusion and aspiration cycle.

It will be evident that there are numerous aspects of this invention which have not been specifically set forth above but which are clearly within the scope and spirit of the invention. The above description is therefore intended to be exemplary only and the invention is to be limited solely by the appended claims.

We claim:

1. A composition for the dissolution of cholesterol gallstones which comprises a synergistically effective mixture of monooctanoin and diethyl ether, wherein said composition has a viscosity of not more than 7 cp and a boiling point greater than 35° C.

2. A composition as in claim 1 having a monooctanoin:diethyl ether volumetric ratio in the range of from about 10:90 to about 70:30.

3. A composition as in claim 2 having said ratio in the range of from about 10:90 to about 50:50.

4. A composition as in claim 3 having said ratio of about 30:70.

5. A composition as in claim 1 have a boiling point of at least 37.5° C.

6. A composition as in claim 1 having a viscosity of not more than 5 cp.

7. A composition as in claim 6 having a viscosity of not more than 2 cp.

8. A method of treating a patient having common bile duct cholesterol calculi which comprises infusing into the biliary tract of said patient a composition comprising a synergistically effective mixture of monooctanoin and diethyl ether, wherein said composition has a viscosity of not more than 7 cp and a boiling point greater than 35° C.

9. A method as in claim 8 wherein said infusion comprises passing said composition into said biliary tract with a high flow rate low pressure pump.

10. A method as in claim 8 wherein said composition has a monooctanoin:diethyl ether volumetric ratio in the range of from about 10:90 to about 65:35.

11. A method as in claim 10 wherein said ratio is in the range of from about 10:90 to about 50:50.

12. A method as in claim 11 wherein said ratio is about 30:70.

13. A method of dissolving common bile duct cholesterol calculi which comprises contacting said calculi with a composition comprising a synergistically effective mixture of monooctanoin and diethyl ether, wherein said composition has a viscosity of not more than 7 cp and a boiling point greater than 35° C.

14. A method as in claim 13 wherein said composition has a monooctanoin:diethyl ether volumetric ratio in the range of from about 10:90 to about 65:35.

15. A method as in claim 14 wherein said ratio is in the range of from about 10:90 to about 50:50.

16. A method as in claim 15 wherein said ratio is about 30:70.

* * * * *

UNITED STATES PATENT AND TRADEMARK OFFICE
CERTIFICATE OF CORRECTION

PATENT NO.  :   4,910,223

DATED       :   March 20, 1990

INVENTOR(S) :   Alan F. Hofmann, et al.

It is certified that error appears in the above-identified patent and that said Letters Patent is hereby corrected as shown below:

On the title page, item [75], the inventors should be as follows:

ALAN F. HOFMANN and
SALAM F. ZAKKO

Signed and Sealed this

Twentieth Day of August, 1991

Attest:

HARRY F. MANBECK, JR.

Attesting Officer

Commissioner of Patents and Trademarks